United States Patent [19]

Tharel

[11] Patent Number: 4,560,380
[45] Date of Patent: Dec. 24, 1985

[54] DISPOSABLE THERAPY DIAPER

[75] Inventor: Morene J. Tharel, Rio Rico, Ariz.

[73] Assignee: Flare Products, Inc., Nogales, Ariz.

[21] Appl. No.: 427,703

[22] Filed: Sep. 29, 1982

[51] Int. Cl.$^4$ .............................................. A61F 13/16
[52] U.S. Cl. ................................ 604/385 R; 604/392
[58] Field of Search ................ 604/385, 347, 348–353,
604/392, 387, 393, 394

[56] References Cited

U.S. PATENT DOCUMENTS

| Re. 26,151 | 1/1967 | Duncan et al. | 604/385 |
|---|---|---|---|
| 3,170,461 | 2/1965 | Watts | 128/139 |
| 3,481,337 | 12/1969 | Ruffo | 604/385 |
| 3,561,446 | 2/1971 | Jones | 604/385 |
| 3,653,382 | 4/1972 | Easley et al. | 604/385 |
| 3,731,688 | 5/1973 | Litt et al. | 604/385 |
| 3,874,385 | 4/1975 | Gellert | 604/385 |
| 3,882,870 | 5/1975 | Hathaway | 604/385 |

*Primary Examiner*—C. Fred Rosenbaum
*Assistant Examiner*—S. Vinyard
*Attorney, Agent, or Firm*—Weiss & Holloway

[57] ABSTRACT

This disclosure relates to a disposable therapy diaper which incorporates non-woven, hypo-allergenic materials including an absorbent layer and incorporates shaping, reservoir and attachment means, to serve as a device for containment of incontinent body wastes during phototherapy, such as hyperbilirubenemia phototherapy of premature infants, so that a desirably large percentage of the phototherapy recipient's skin surface is exposed to the therapeutic photoradiation, while the excess body wastes produced during such phototherapy are contained with minimal skin irritation to the phototherapy recipient.

This disclosure also relates to a manufacturing method for the disposable therapy diaper which incorporates the cutting and assembly of various layers of structural and absorbent non-woven, hypo-allergenic materials and the heat sealing thereof, to serve as an economical and efficient manufacturing process so that cost of the disposable therapy diaper may be minimized while retaining desirable, structural qualities thereof.

1 Claim, 6 Drawing Figures

U.S. Patent  Dec. 24, 1985  4,560,380
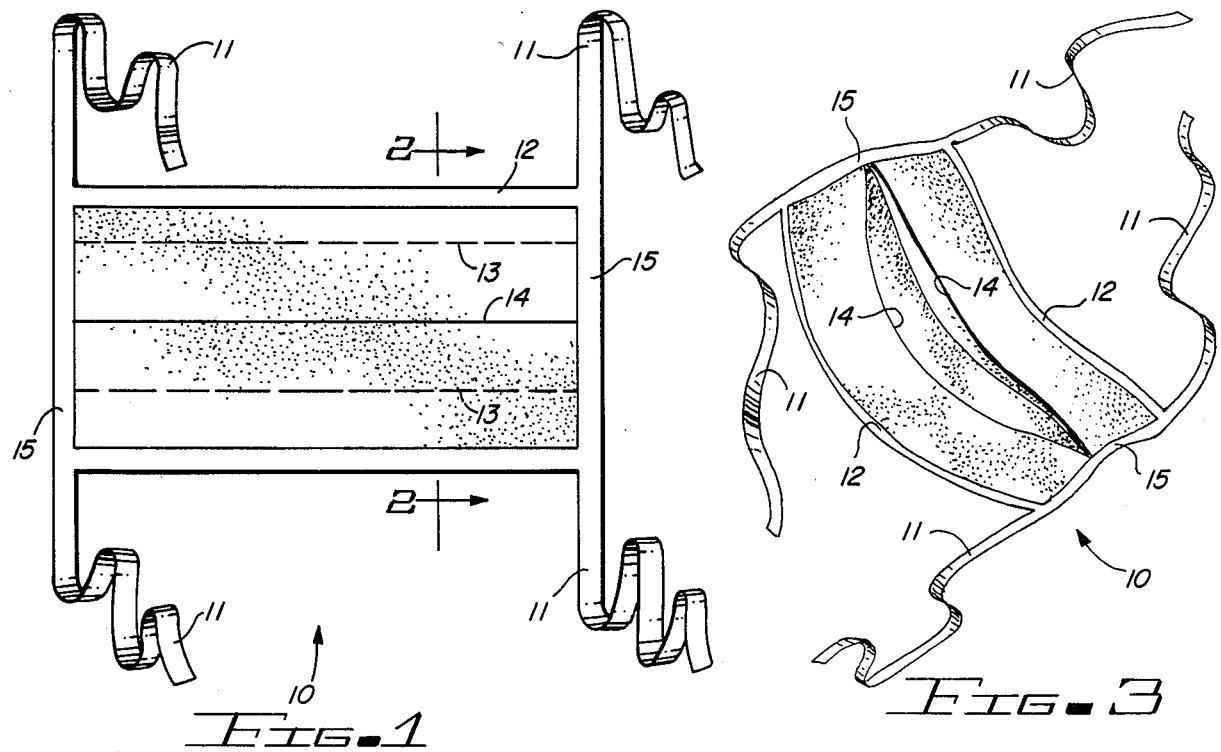
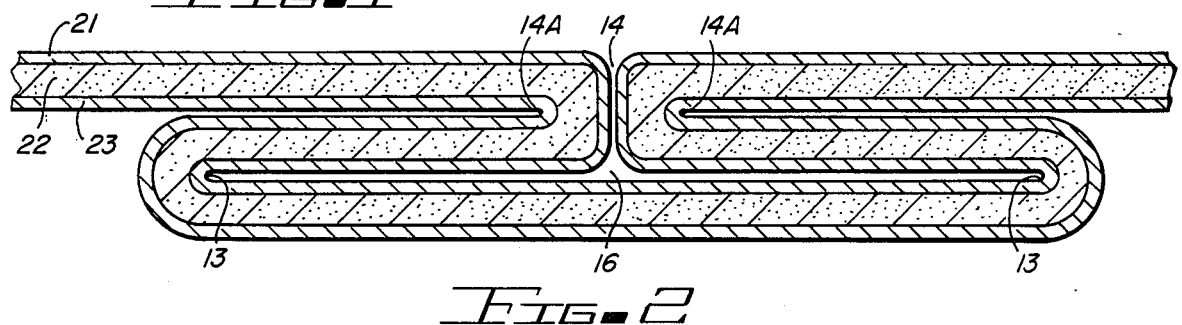
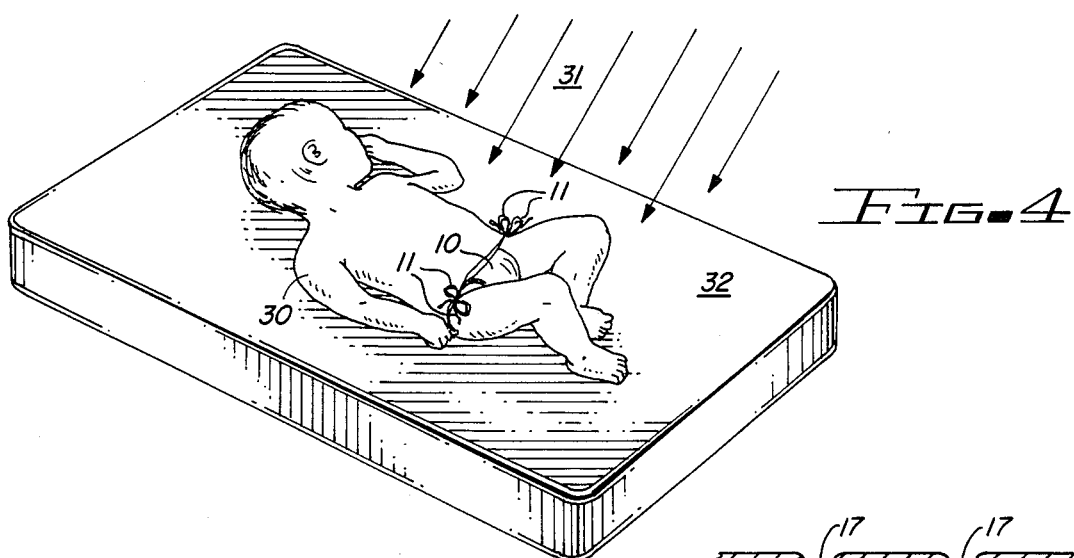
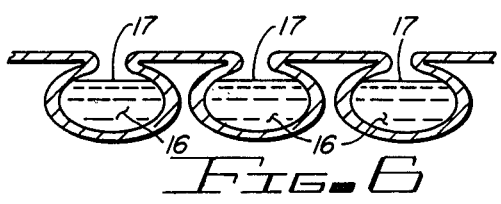

DISPOSABLE THERAPY DIAPER

BACKGROUND OF THE INVENTION

1. Field of the Invention

This invention relates generally to diapers for the containment of body wastes, and more specifically, to disposable therapy diapers for use during phototherapy of incontinent persons.

2. Description of the Prior Art

In the past, persons, especially tiny premature infants, requiring skin photo-irradiation therapy who were incontinent were usually clothed in ordinary diapers or waterproof pants having close-fitting, elastic openings, for the retention of the excess quantities of urine and body wastes which were naturally secreted during such phototherapy. It is desirable that at least ninety percent of body skin area be exposed to such phototherapy; however ordinary diapers and other waste retention means heretofore available have been relatively large or bulky, and have therefore reduced the percentage of exposed skin surface below the desirable 90% amount. In the case of hyperbilirubenemia phototherapy of premature infants, prior-art diapers and pants not only covered an excessive percentage of skin area, but sometimes have contributed to irritation of or to an allergic reaction with the highly sensitive premature infant's skin.

Various means of fastening have been used for such diapers and pants, including safety pins, clips, and straps or ties. When strap or tie fasteners have been used and attached to the diapers or pants, attachment has been typically achieved by sewing means, and such fastener attachment constituted a substantial portion of the manufacturing cost of the diapers or pants.

A need existed for a disposable therapy diaper covering a minimal percentage of skin area, but yet be capable of substantial absorption and retention of excess body wastes.

A need also existed for a disposable therapy diaper comprising non-irritating and hypo allergenic materials.

A need further existed for a manufacturing method for a disposable therapy diaper which combined low assembly cost with the imparting of desirable structural qualities such as strength, shaping and absorptivity.

BRIEF DESCRIPTION OF THE DRAWINGS

FIG. 1 is a top view of the disposable therapy diaper showing the securing straps or ties.

FIG. 2 is a cross section view taken along lines 2—2 of FIG. 1, in the direction of the arrows showing the multipleplies of structural and absorbent material and the folds forming a reservoir for body waste.

FIG. 3 is a perspective view of the disposable therapy diaper showing conformance to the body of the wearer and the parting folds permitting body waste flow into the reservoir.

FIG. 4 is a perspective view of the disposable therapy diaper in use during phototherapy, showing how the straps or ties permit securing of the bikini type diaper to the wearer and also showing how this diaper is used to provide minimum skin coverage.

FIG. 5 is a cross section view of another embodiment of the invention wherein the diaper of FIG. 1 contains a plurality of folds forming a plurality of reservoirs, showing the reservoirs in a flattened, empty condition.

FIG. 6 is a cross section view in accordance with FIG. 5 showing the reservoirs partially filled and expanded with liquid or solid body waste.

SUMMARY OF THE INVENTION

In accordance with one embodiment of this invention, it is an object of this invention to provide an improved diaper.

It is another object of this invention to provide an improved disposable therapy diaper.

It is a further object of this invention to provide an improved disposable therapy diaper having body waste absorption and containment means.

It is still another object of this invention to provide an improved disposable therapy diaper having at least one folded expandible reservoir for the retention of excess body waste.

It is yet another object of this invention to provide an improved disposable therapy diaper which combines efficient body waste absorption and retention with minimal skin area coverage, for use in phototherapy.

Still another object of this invention is to provide an improved disposable therapy diaper, having a wearer surface which is non-irritating and hypo-allergenic.

Yet another object of this invention is to provide an improved disposable therapy diaper having straps or ties for attachment to the wearer.

In accordance with another embodiment of this invention, in addition to the objects desired for the first embodiment, it is an object of this invention to provide an improved disposable therapy diaper having a plurality of folded expandible reservoir means for the retention of excess body waste.

In accordance with both the first and second embodiments of this invention, it is an object of this invention to provide an improved method of manufacture of a disposable therapy diaper in which diaper edges and straps are affixed to each other by heat-sealing means.

DESCRIPTION OF THE PREFERRED EMBODIMENTS

In accordance with one embodiment of this invention, a diaper is disclosed which comprises a fluid absorbing diaper portion, and folded expandible reservoir means located in said diaper portion for providing a reservoir for holding body waste material.

In accordance with another embodiment of this invention, a disposable therapy diaper is disclosed which comprises a fluid absorbing diaper portion, and a plurality of folded expandible reservoir means for providing a plurality of reservoirs for holding body waste material.

In accordance with both of the above embodiments of this invention, a method of manufacturing a disposable therapy diaper is disclosed which comprises the steps of inserting at least one layer of absorbent material beween outer layers of hypo-allergenic, non-woven material forming a reservoir for body waste bounded by an outside, surface portion of one of said outer layer of hypo-allergenic, non-woven material, placing strips of hypo-allergenic, non-woven material along the edges of said outer layers for the formation of attachment straps, and heat-sealing the periphery of said outer layers and the portions of said strips in contact with said outer edges.

The foregoing and other objects, features and advantages will be apparent from the following, more particular, description of the preferred embodiments of the invention, as illustrated in the accompanying drawings.

THE SPECIFICATION

Referring to FIG. 1, a top view, which is the "inside" surface contacting the body of a wearer, of a disposable therapy diaper 10 is shown. Straps 11 are used to attach the diaper to its wearer. Edges of the diaper 12 and 15 are heat-sealed, and straps 11 are simultaneously attached by the same heat-seal means to edges 15. In a first embodiment, a single central opening 14 provides access to a folded extensible reservoir below opening 14, the limits of which are delineated by dotted lines 13 signifying folds. Reference line 2—2 is provided for clarity in subsequent figures.

Referring to FIG. 2, a cross-sectional view along reference line 2—2 shown in FIG. 1, of the folded extensible reservoir region 16 of the disposable therapy diaper 10 is shown, in which may be seen opening 14 which is formed by folds 14A, folds 13 which define the lateral limits of reservoir 16, and a "sandwich" of absorbent material 22 between layers of soft, hypo-allergenic, non-woven material, 21 and 23.

FIG. 2 illustrates five rectangular portions comprising the diaper and the reservoir means:

a first portion extending from upper left of FIG. 2 to the left-hand fold 14A;

a second portion connected to the first portion and extending from the left-hand fold 14A to the left-hand fold 13;

a third portion connected to the second portion and extending from the left-hand fold 13 to the right-hand fold 13;

a fourth portion connected to the third portion and extending from the right-hand fold 13 to the right-hand fold 14A; and a fifth portion connected to the fourth portion and extending from the left-hand fold 14A to the upper right of FIG. 2.

Referring to FIG. 3, a perspective view is shown of the disposable therapy diaper 10 partially conformed to a wearer's body, illustrating how a reservoir 16 is formed by distension of folds 14A.

Referring to FIG. 4, a perspective view is shown of the disposable therapy diaper 10 in use, attached by tying straps 11 about the waist of wearer 30. The diaper permits maximum exposure of wearer 30 skin area to impinging phototherapy radiation 31, while preventing soiling of mattress surface 32.

Referring to FIG. 5, a cross-sectional view along sectional line 2—2 is shown of a second embodiment of the disposable therapy diaper, in which a plurality of folded expansible reservoirs are illustrated in dry, collapsed position.

Referring to FIG. 6, a cross-sectional view along sectional line 2—2 is shown of the embodiment of FIG. 5, illustrating the filling of reservoirs 16 with body waste liquid or solid 17.

While the invention has been particularly shown and described with reference to preferred embodiments thereof, it will be understood by those skilled in the art that the foregoing and other changes in form and details may be made therein without departing from the spirit and scope of the invention.

I claim:

1. A disposable therapy diaper for infants, comprising:

a front portion, a rear portion and two side portions connecting said front and rear portions, said front and rear portions adapted to contact the waist of an infant and said side portions adapted to go between the legs of the infant, each of said side portions being longer than each of said front and rear portions, said front, rear and side portions providing a fluid absorbing generally rectangular-shaped diaper portion including at least two layers of hypo-allergenic, non-woven material and at least one layer of soft, absorbent material sandwiched between said layers of hypo-allergenic, non-woven material, said fluid absorbing generally rectangular-shaped diaper portion being of minimum area so that only a minimum amount of skin area of a wearer is covered during therapy, said layers of hypo-allergenic, non-woven material having heat sealed outer peripheries;

at least one folded expansible reservoir means located in said generally rectangular-shaped diaper portion for providing a reservoir for holding urinal and fecal body waste material, each of said folded expansible reservoir means disposed substantially parallel to said side portions and substantially perpendicular to said front and rear portions and including:

(a) a first edge portion, (b) a first rectangular portion which extends in a first direction perpendicular to said first edge portion to a downward first fold line, said downward first fold line being parallel to said first edge portion, (c) a second rectangular portion connected to said first rectangular portion and extending in a second direction to a downward second fold line, said downward second fold line being parallel to said downward first fold line and located between said downward first fold line and said first edge portion, (d) a third rectangular portion connected to said second rectangular portion and extending from said downward second fold line to an upward third fold line, said upward third fold line being parallel to said downward second fold line, one length of said third rectangular portion being approximately twice the corresponding length of said second rectangular portion, (e) a fourth rectangular portion connected to said third rectangular portion and extending from said upward third fold line to a fourth upward fold line, said fourth upward fold line being parallel to said third upward fold line, one length of said fourth rectangular portion being approximately equal to the corresponding length of said second rectangular portion, and (f) a fifth rectangular portion connected to said fourth rectangular portion and extending from said fourth upward fold line to a second edge portion, said second edge portion being parallel to said upward fourth fold line, and one length of said fifth rectangular portion being approximately equal to the corresponding length of said first rectangular portion; and two continuous thin strap means of generally equal length heat sealed to said front and rear portions, respectfully, of said generally rectangular-shaped diaper portion and extending across each of said front and rear portions of said diaper portion for attaching said diaper portion to the infant in order to partially cover the buttock and genitalia of the infant by tying end portions of one of said two continuous thin strap means to end portions of the other of said two continuous thin strap means, said two continuous thin strap means being made out of a hypo-allergenic, non-woven material, each one of said two continuous thin strap means having a portion heat sealed to one of said front and rear portions of said generally rectangular-shaped dia- per portion for permanently securing end portions of each of said folded expansible reservoir means to maintain a fixed pleated configuration.

* * * * *